United States Patent [19]
Rudy, Jr. et al.

[11] Patent Number: 5,593,382
[45] Date of Patent: Jan. 14, 1997

[54] EXTRICATION CERVICAL COLLAR WITH ADJUSTABLE SUPPORTS

[76] Inventors: Ronald M. Rudy, Jr., 10728 Kasmir Ct., Boynton Beach, Fla. 33437; Freddy T. Lee, 1502 SW. 22nd Ave., Boynton Beach, Fla. 33426

[21] Appl. No.: 314,653

[22] Filed: Sep. 29, 1994

[51] Int. Cl.⁶ ..................................................... A61F 5/00
[52] U.S. Cl. ............................................................ 602/18
[58] Field of Search ................................. 602/17, 18, 19, 602/32, 33, 34, 35; 128/DIG. 23, 23

[56] References Cited

U.S. PATENT DOCUMENTS

| | | |
|---|---|---|
| 2,904,040 | 9/1959 | Hale .......................................... 602/18 |
| 3,724,452 | 4/1973 | Nitschke .................................... 602/18 |
| 4,515,153 | 5/1985 | Calabrese .................................. 602/18 |
| 4,582,051 | 4/1986 | Greene et al. . |
| 4,628,913 | 12/1986 | Lerman . |
| 4,677,969 | 7/1987 | Calabrese .................................. 602/18 |
| 4,712,540 | 12/1987 | Tucker et al. . |
| 5,010,877 | 4/1991 | Druskoczi ................................. 602/18 |
| 5,058,572 | 10/1991 | Schmid ..................................... 602/18 |
| 5,180,361 | 1/1993 | Moore et al. ............................. 602/18 |
| 5,215,517 | 6/1993 | Stevenson et al. ....................... 602/18 |
| 5,230,698 | 7/1993 | Garth ........................................ 602/18 |

FOREIGN PATENT DOCUMENTS 918770  2/1955  Denmark .................................. 602/18

Primary Examiner—Richard J. Apley
Assistant Examiner—Kim M. Lee
Attorney, Agent, or Firm—Oltman Flynn & Kubler

[57] ABSTRACT

A surgical collar for emergency rescues has mandibular and occipital supports that will each adjust vertically without affecting the other.

10 Claims, 3 Drawing Sheets

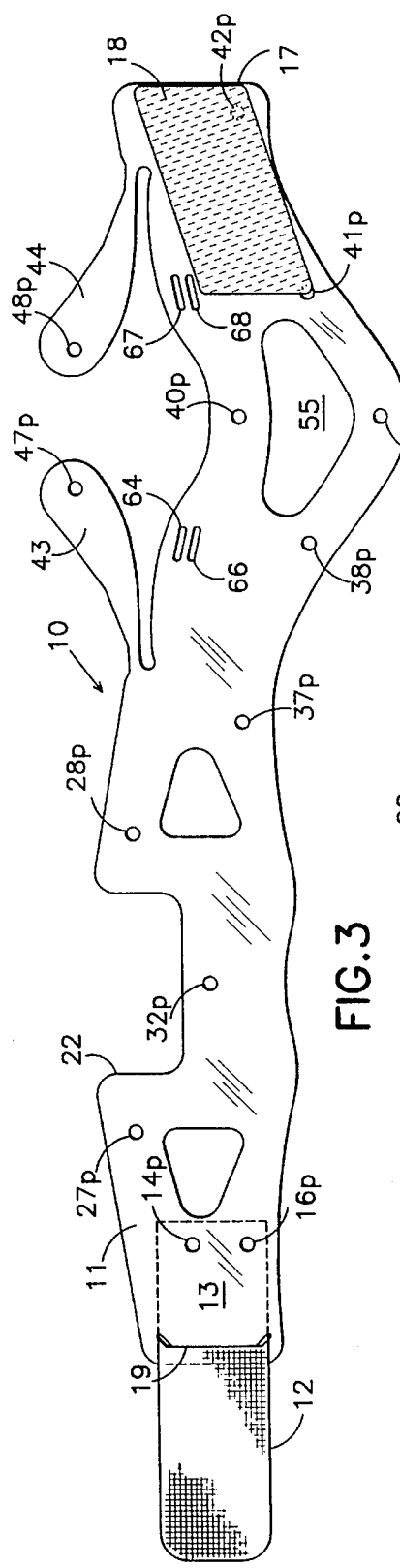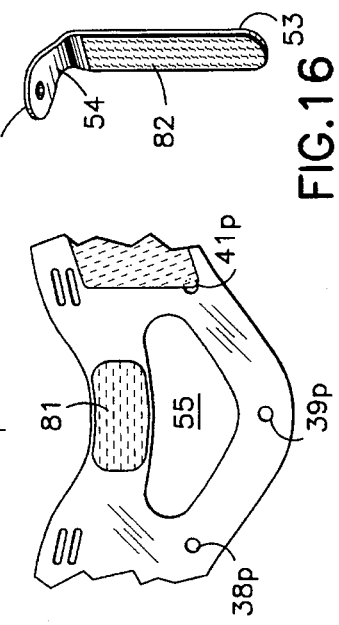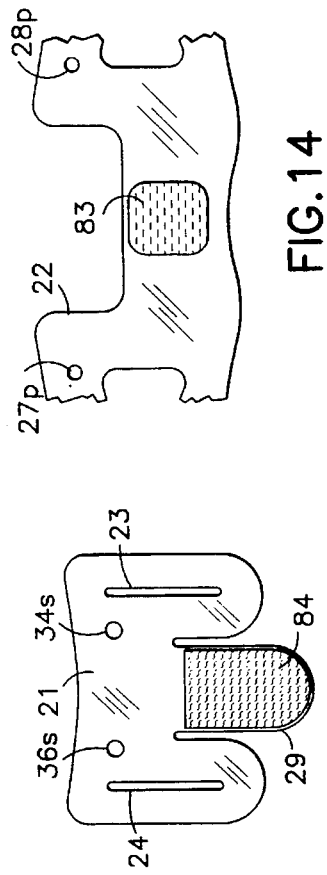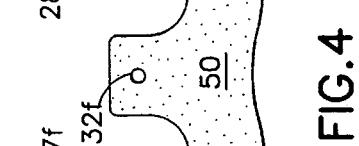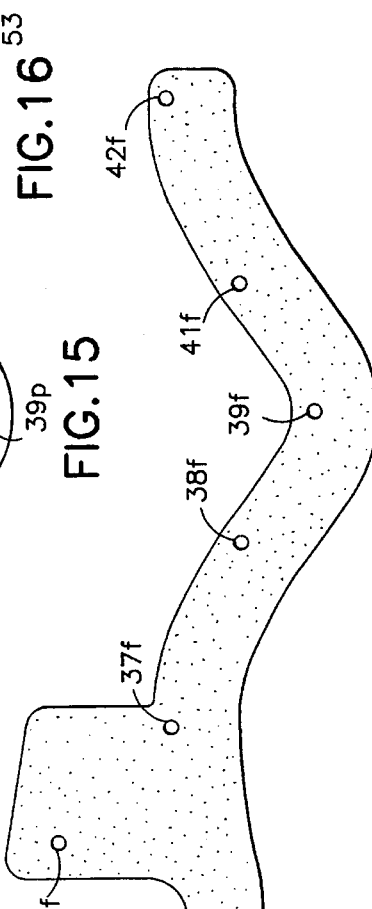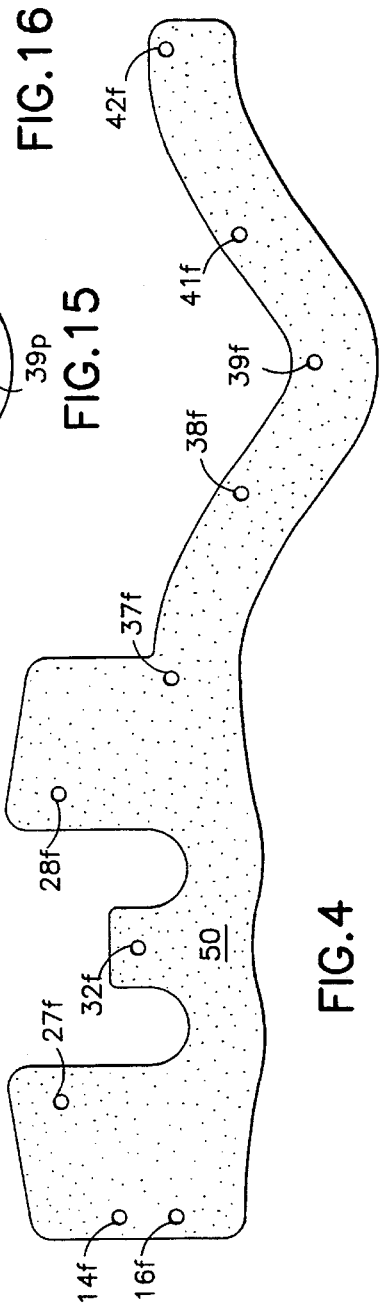

EXTRICATION CERVICAL COLLAR WITH ADJUSTABLE SUPPORTS

BACKGROUND OF THE INVENTION

In rescue operations where, typically, the rescuers must move victims from an accident site to a waiting ambulance or truck they must protect the upper spinal columns of said victims with emergency cervical collars before moving them. Rescue vehicles routinely carry cervical collars of three or four different neck lengths and a rescuer must carry several of these different-sized cervical collars when he first runs from the vehicle to the location of the victim. We have, herein, made the distances from the collar proper to the occipital and mandibular support body contacts, adjustable, so that vehicles need carry only one size of cervical collar.

U.S. Pat. No. 4,712,540 describes a cervical collar that lies flat in storage but in which the chin support automatically twists into a transverse position when the collar expands to its cylindrical form. However the patent describes no means for adjusting the elevation of the chin support.

U.S. Pat. No. 3,916,885 describes a cervical collar made up of two overlapping cylindrical bands where two frontal VELCRO-tipped straps can adjust their relative positions. These adjustments affect the whole upper band, however. They cannot adjust the occipital and mandibular supports altogether independently.

U.S. Pat. No. 4,582,051, like the above, also comprises upper and lower cylindrical bands and VELCRO means for adjusting the distance between them. Here they position the adjusting means front and back center and the adjustment of either means moves the entire upper band. The patentees disclose no means for adjusting occipital and mandibular supports independently.

SUMMARY OF THE INVENTION

We have invented a cervical collar, particularly for use in rescue operations, comprising independently adjustable mandibular and occipital supports. The collar comprises a single stiff wide band to which the mandibular and occipital supports attach in a vertically adjustable assembly. The structural elements of our collar comprise 1.5 mm high density polyethylene sheeting with sheets of resilient plastic foam cushioning riveted on the inside surfaces of the structural elements wherever they may contact the patient.

In a preferred embodiment the mandibular support comprises three aligned, downwardly projecting, stiff straps, the central of which has perforations that fit an adjusting pin projecting from a lower portion of the supporting band, and the other two of which wedge into rectangular slots in the same band. These straps adjust, not only the overall elevation of the mandibular support, but its transverse angle. Instead of a perforated strap for the central support we also employ a stiff plastic rod, along with a plastic or metal spring clip, attached to the band through the rod passes.

Preferably the immediate contacting element of the mandibular support forms a trough-like member curved to accept a human chin. We have determined that the appropriate curve will result from cutting the desired shape into the surface of the plastic and then making a 90 deg. bend in the plastic sheeting. We do not require heat or a molding die.

BRIEF DESCRIPTION OF THE DRAWING

FIG. 3 shows a flattened plan of the unassembled plastic band of our invention.

FIG. 4 shows plan of the foam cushioning cutout attachable to the plastic band of FIG. 3.

FIG. 13 shows a modification of the occipital support of FIG. 5, in reverse view.

FIG. 14 shows an elevation of a modification of the area below the relief 22 of the plastic band 11, to cooperate with the modification of FIG. 13.

FIG. 15 shows VELCRO patch for locking the mandibular support.

FIG. 16 shows an alternative construction of the tongue 53.

DETAILED DESCRIPTION OF A PREFERRED EMBODIMENT

Figure 1:
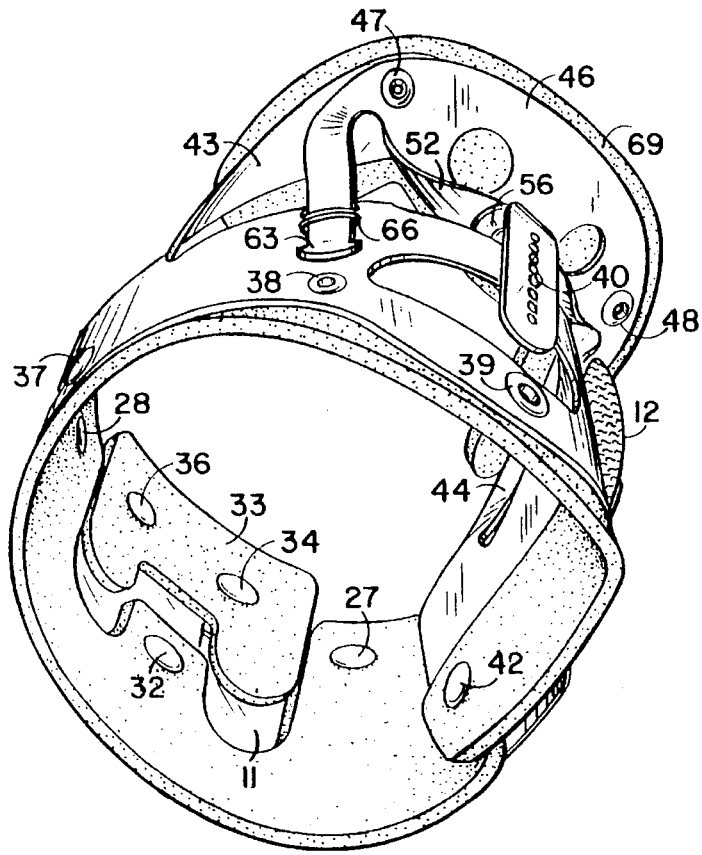
FIG. 1 shows a frontal perspective view of the cervical collar of our invention, obliquely from below.
Figure 5:
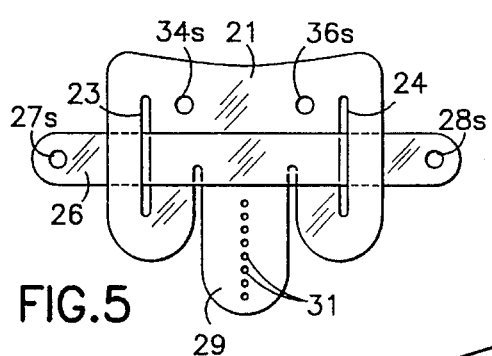
FIG. 5 shows an elevation of the occipital plastic support of our invention.

Referring first to FIG. 1, and to FIG. 3 where the band lies flat, with its inside surface down, our improved cervical collar 10 comprises a plastic band 11 about 3½ inches (9 cm) wide and bent into a cylindrical shape held closed by a VELCRO strip 12, extending from an occipital end 13 of the band 11 to which we have fastened it by plastic rivets through rivet holes 14p, 16p to a mandibular end 17 which has a VELCRO strip 18 cemented to it. The strip 12 fastens to the inside of the collar and passes to the outside through a slot 19 at the occipital edge of the band 11. A plastic occipital support 21 (FIG. 5) comprises, preferably, the same type of plastic sheeting as the band 11, for which we prefer high-density polyethylene, 0.06 in. (1.5 mm) thick. The plastic band 11 (FIG. 3) comprises additional rivet holes 27p, 28p, 32p, 37p, 38p, 39p, 40p, 41p, 42p, 47p, and 48p for like-numbered rivets and comprises a triangular opening 55 above the rivet hole 39f, that remains unobstructed by the cushioning 50; for a possible tracheostomy.

The occipital support 21 fits within the dimensions of a relief 22 cut into the upper edge of the band 11 and has two vertical guide slots 23, 24 for a horizontal strap 26 that attaches to the band 11 by through two rivet holes 27s, 28s to span the relief 22. A central portion of the support 21 extends downwardly in a tongue 29 with a vertical line of perforations 31—31 that fit an adjusting pin 32, projecting from the band 11, to set the occipital support 21 at a desired height. We obtained the plastic rivets referred to herein from commercial sources which continue to sell them widely for connecting plastic and similar sheeting. However other means of connection such as cementing, sewing, and stapling will also come within the scope of our invention.

Figure 2:
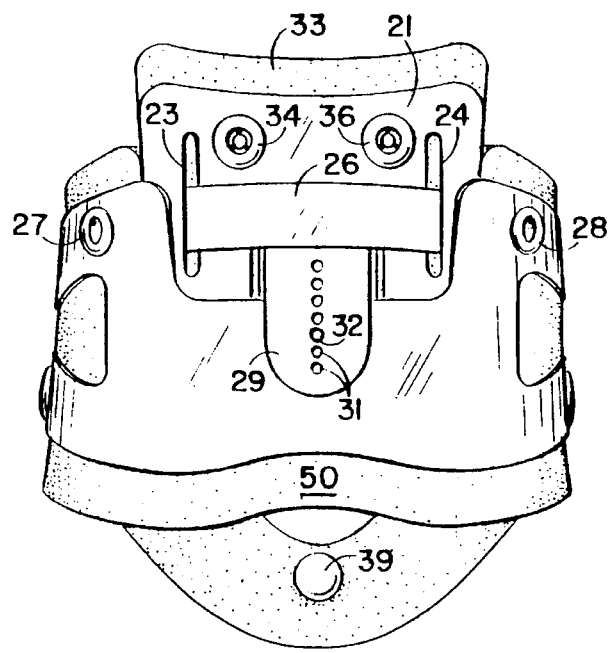
FIG. 2 shows a rear elevation of the cervical collar of our invention.

Conventional plastic rivets 27, 28, 32, 34, 36, 37, 42, and 48 appear in FIG. 1 and rivets 27, 28, 34, 36, and 39 appear in FIG. 2. The numerals of these rivets correspond to the number portions of the numerals marking the rivet holes they are intended for in the other FIGURES.

Figure 6:
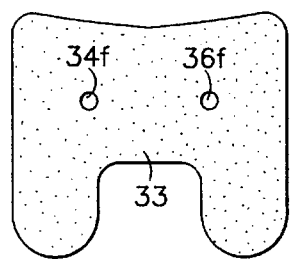
FIG. 6 shows an elevation of the foam cushioning cutout attachable to the support of FIG. 5.
Figure 12:
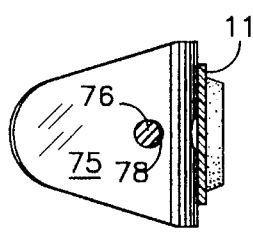
FIG. 12 shows a sectional view through the line 12—12 of FIG. 8.

In FIG. 6 we show a sheet of plastic foam cushioning 33 cut out to fit the occipital support 21 to which it fastens through rivet holes 34f, 36f so that it extends about 0.5 inch (13 mm) above the top edge of the support 21. Also, in FIG. 4 we have shown a long strip of plastic foam cushioning 50 to match the band 10 so that the cushioning extends about 0.6 in. (15 mm) below the hard plastic of the band. The cushioning attaches to the band through rivet holes 14f, 16f, 27f, 28f, 37f, 38f, 39f, 41f, and 42f.

Two attachment straps 43, 44, integral therewith (FIG. 3), attach a mandibular support 46 to the band 11 by means of rivets (47, 48 FIG. 1), through rivet holes 47p, 48p with the straps 43, 44 twisted to make the mandibular support, a.k.a. chin rest, horizontal. We score a curve about 0.03 in. (0.8 mm) deep in the upper surface of the chin receiving portion 49 and then bend down a lower arc 52 of the support 46 to form a right angle. This forces the surface 49 to form a dihedral curve with the surface of arc 52 that equals the scored curve 51. This require no tools, dies or heating other than a scoring blade and an edge defining the curve 51.

Figure 7:
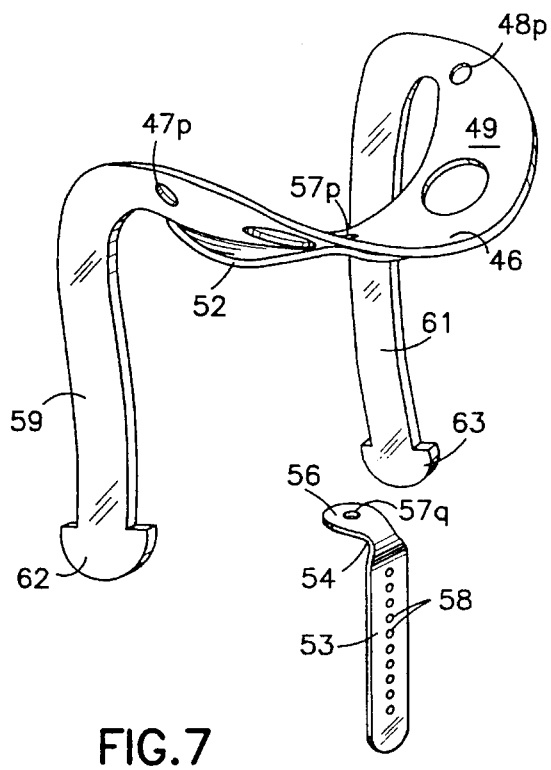
FIG. 7 shows an exploded perspective view of the mandibular support of our invention.

A tongue 53 (FIG. 7) comprising a neck portion 54 and attachment nodule 56 fastens to the underside of the mandibular support 46 by means of a rivet 57. The tongue 53 comprises a line of perforations 58—58 that lock onto a pin protruding from the center of the rivet 39; and two strap-like elongations 59, 61 of the mandibular support 46, comprising respective sharp-edged expansions 62, 63 pass in and out of two pairs 64, 66 and 67, 68 of slots in the band 11 with sufficient friction to keep the mandibular support 46 at any desired side to side angle, usually 180 deg. A shaped pad 69 with long side projections 71, 72 cushions the upper surface 49 of the mandibular support 46 with the side projections extending over the straps 43, 44. The rivet 49 and side rivets 73, 74 secure the pad 69 to the mandibular support 49.

Essentially the construction of our cervical collar requires only two basic materials, 0.06 inch high density polyethylene sheeting and rolls of foam cushioning about ¼ inch thick. We have used a polyolefin foam called Volada from the Voltek division of Sekisui America Corp. but do not wish to limit our invention thereto. Many commercial sources make VELCRO widely available.

Figure 8:
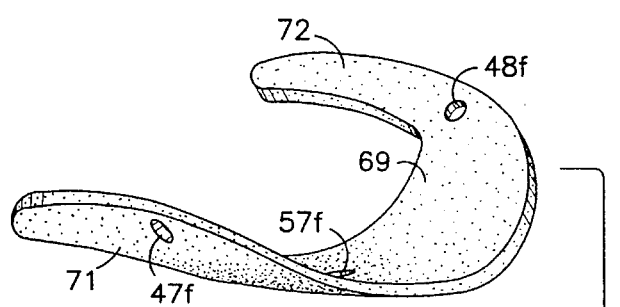
FIG. 8 shows an elevation of an alternative mandibular support of our invention.
Figure 9:
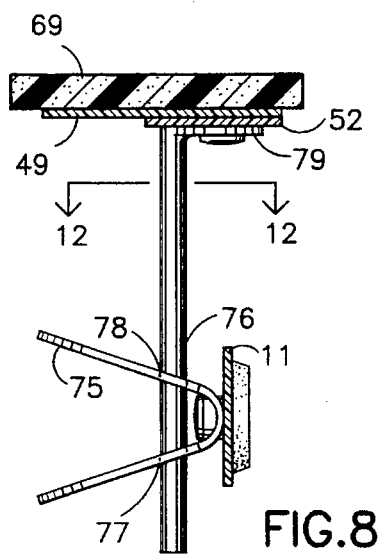
FIG. 9 shows a plan of the mandibular support 46 from above prior to forming its curved shape.

In FIG. 8 we have shown an alternative means for vertically fixing the elevation of the mandibular support 49. A plastic rod 76, comprising an intergral upper 90 deg. attachment shelf 79, projects downwardly from the lower surface of the mandibular support 46 and passes through openings in walls 77, 78 of a plastic or metal spring clip 75 that attaches to the band 11, and in FIGS. 15 and 16 another of such alternative means, wherein we have fixed a VELCRO patch 81 onto the band 11 above the tracheoscomy opening 55, and a matching patch 82 onto the tongue 53. We have also invented an alternative means for fixing the occipital adjustment, by affixing a VELCRO patch 83 onto the band 11 under the relief 22 (FIG. 14) and a matching patch 84 onto the facing side of the tongue 29 of the support 21.

Figure 10:
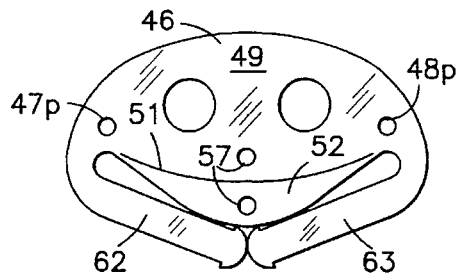
FIG. 10 shows a section through a prior art rivet used to assemble our invention.
Figure 11:
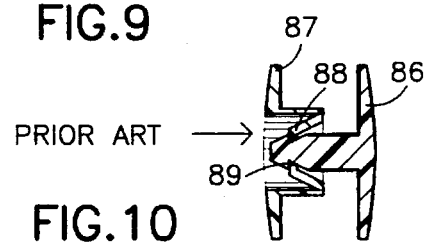
FIG. 11 shows a sectional view of a novel holding pin usable with the rivets of FIG. 10.

FIG. 10 illustrates a section of a commercially available plastic rivet having a plug 86 and a female portion comprising a snap 87. Prongs 88 of the snap 87 fit into a sharp-edged groove 89 of the plug 86 with a permanent grip. We have discovered that we can fashion pins to secure the straps 53 and 31 of the mandibular and occipital supports respectively by elongating shanks 91 (FIG. 11) of plastic plugs to have an annular depression 92 and bulb 93 that will protrude from conventional rivets where gripping-pins are required.

We present the foregoing description as exemplary rather than definitive of our invention for which we desire an award of letters patent as defined by the appended claims.

We claim:

1. An extrication cervical collar suitable for rescue operations comprising:
   (A) a single wide band in the form of a loop of supporting material of sufficient length to surround the neck of a patient,
   (B) a mandibular support extending upwardly from said band, said mandibular support comprising a substantially horizontal surface component, and
   (C) a plurality of spaced-apart structural members adjustably and independently supporting said mandibular support from said band at a distance required for the length of the neck of said patient, wherein;
      (i) a central of said structural members comprises a first stiff strap extending downwardly from said mandibular support,
      (ii) said first strap comprises a vertical row of perforations therethrough,
      (iii) said band supports a pin projecting forwardly therefrom and fitable snugly into said perforations,
      (iv) the remaining two of said structural members comprise second and third stiff straps that extend downwardly from either side of said first strap, and
      (v) said band comprises two pairs of essentially rectangular openings therein for engaging said second and third structural members to level said mandibular support.

2. The cervical collar of claim 1 wherein said plurality of spaced-apart structural members equals three members.

3. The cervical collar of claim 1 comprising an independently movable occipital support and means independently and adjustably connecting said occipital support to said band as required by the length of the neck of said patient.

4. The cervical collar of claim 3 comprising a plurality of sheets of plastic foam cushioning on the surfaces of said band, said mandibular support, and said occipital support contacting said patient.

5. The cervical collar of claim 3 wherein said occipital support comprises walls defining two spaced-apart vertical slots, said cervical collar comprises a horizontal strap mounted across a rear portion of said band, and said strap passes through said slots, thereby securing said occipital support to said band.

6. The cervical collar of claim 1 wherein said band of supporting material comprises high-density polyethylene about 0.06 inches (1.5 mm) thick.

7. The cervical collar of claim 1 wherein said mandibular support curves upwardly ahd permanently around a central lengthwise axis.

8. The method of forming the upward curve in the mandibular support of claim 7 comprising the steps of inscribing said curve in the form of a cut of about ½ its thickness in the material of said mandibular support, and downwardly bending said mandibular support at said inscribed curve, thereby curving said mandibular support without the need for a shaping die.

9. An extrication cervical collar suitable for rescue operations comprising:

(A) a single wide band in the form of a loop of supporting material of sufficient length to surround the neck of a patient, (B) a mandibular support extending upwardly from said band, said mandibular support comprising a substantially horizontal surface component, and (C) a plurality of spaced-apart structural members adjustably and independently supporting said mandibular support from said band at a distance required for the length of the neck of said patient, wherein:
   (i) a central of said structural members comprises a stiff rod extending downwardly from said mandibular support,
   (ii) said band supports a spring clip comprising perforations for said rod,
   (iii) second and third of said structural members extend downwardly from either side of said first structural member and comprise stiff straps, and
   (iv) said band comprises two pairs of essentially rectangular openings therein for engaging said second and third structural members, thereby leveling said mandibular support.

10. An extrication cervical collar suitable for rescue operations comprising:

(A) a single wide band in the form of a loop of supporting material of sufficient length to surround the neck of a patient, (B) a mandibular support extending upwardly from said band, said mandibular support comprising a substantially horizontal surface component, and (C) a plurality of spaced-apart structural members adjustably and independently supporting said mandibular support from said band at a distance required for the length of the neck of said patient, wherein:
   (i) a central of said structural members comprises a first stiff strap extending downwardly from said mandibular support and a surface facing said band,
   (ii) said cervical collar comprises a first patch of hook and loop fasteners fixed to the inner-facing surface of said strap,
   (iii) said band supports a second patch of hook and loop fasteners facing said first patch of hook and loop fasteners and grippable thereto,
   (iv) the remaining two of said structural members comprise second and third stiff straps that extend downwardly from either side of said first strap, and
   (v) said band comprises two pairs of essentially rectangular openings therein for engaging said second and third structural members to level said mandibular support.

* * * * *